United States Patent
Wong

(10) Patent No.: US 9,709,651 B2
(45) Date of Patent: Jul. 18, 2017

(54) COMPENSATED MAGNETIC RESONANCE IMAGING SYSTEM AND METHOD FOR IMPROVED MAGNETIC RESONANCE IMAGING AND DIFFUSION IMAGING

(71) Applicant: Alexander Sheung Lai Wong, Waterloo (CA)

(72) Inventor: Alexander Sheung Lai Wong, Waterloo (CA)

( * ) Notice: Subject to any disclaimer, the term of this patent is extended or adjusted under 35 U.S.C. 154(b) by 434 days.

(21) Appl. No.: 14/463,887

(22) Filed: Aug. 20, 2014

(65) Prior Publication Data

US 2016/0054420 A1 Feb. 25, 2016

(51) Int. Cl.
  *G01R 33/58* (2006.01)
  *G01R 33/563* (2006.01)
  *G01R 33/56* (2006.01)
  *A61B 5/055* (2006.01)

(52) U.S. Cl.
  CPC ... *G01R 33/56341* (2013.01); *G01R 33/5608* (2013.01); *A61B 5/055* (2013.01); *A61B 2576/00* (2013.01); *G01R 33/58* (2013.01)

(58) Field of Classification Search
  CPC .......... G01R 33/56341; G01R 33/5608; G01R 33/58; A61B 5/055; A61B 2576/00
  See application file for complete search history.

(56) References Cited

U.S. PATENT DOCUMENTS

| | | | |
|---|---|---|---|
| 2015/0253410 A1* | 9/2015 | Warfield | A61B 5/055 324/309 |
| 2015/0272467 A1* | 10/2015 | Warfield | A61B 5/055 382/131 |
| 2015/0371384 A1* | 12/2015 | Wong | G06T 7/0016 382/103 |
| 2016/0195597 A1* | 7/2016 | Huang | G01R 33/50 324/309 |
| 2016/0209487 A1* | 7/2016 | Stern | G01R 33/4806 |
| 2016/0247299 A1* | 8/2016 | Tan | G06T 11/003 |
| 2016/0341810 A1* | 11/2016 | Rich | G01R 33/56316 |

FOREIGN PATENT DOCUMENTS

JP 1912161 A2 * 4/2008 .......... G06K 9/6212

* cited by examiner

*Primary Examiner* — Clayton E Laballe
*Assistant Examiner* — Ruifeng Pu
(74) *Attorney, Agent, or Firm* — Tai W. Nahm; Miller Thomson LLP

(57) ABSTRACT

There is disclosed a novel system and method for improving MRI and DWI image quality and tissue detail and contrast is introduced and referred to in this disclosure as "compensated magnetic resonance imaging" or CMRI in which a compensation function and noise scale factor are determined during a calibration process by acquiring one or more test signals on the MRI system to determine a compensation function and noise scale factor, and signal acquisitions are conducted from a subject, and the signals are then used to reconstruct MRI images by maximizing a quality metric that takes the acquired signals, compensation function, and noise scale factor as part of the input parameters. Advantageously, by taking into a compensation function and a noise scale factor, CMRI can provide significantly improved MRI image quality and tissue detail and contrast.

28 Claims, 12 Drawing Sheets

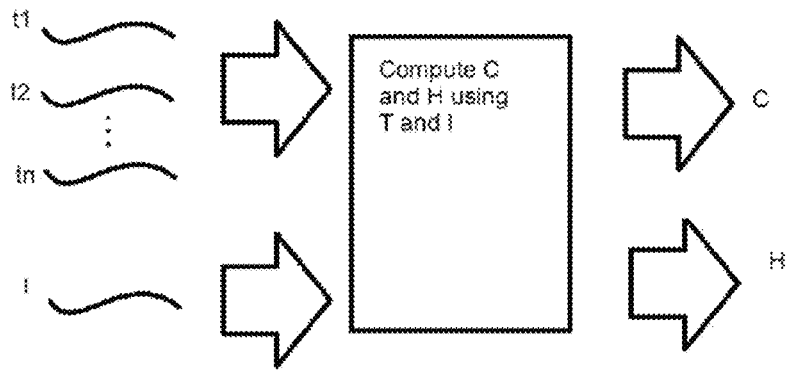
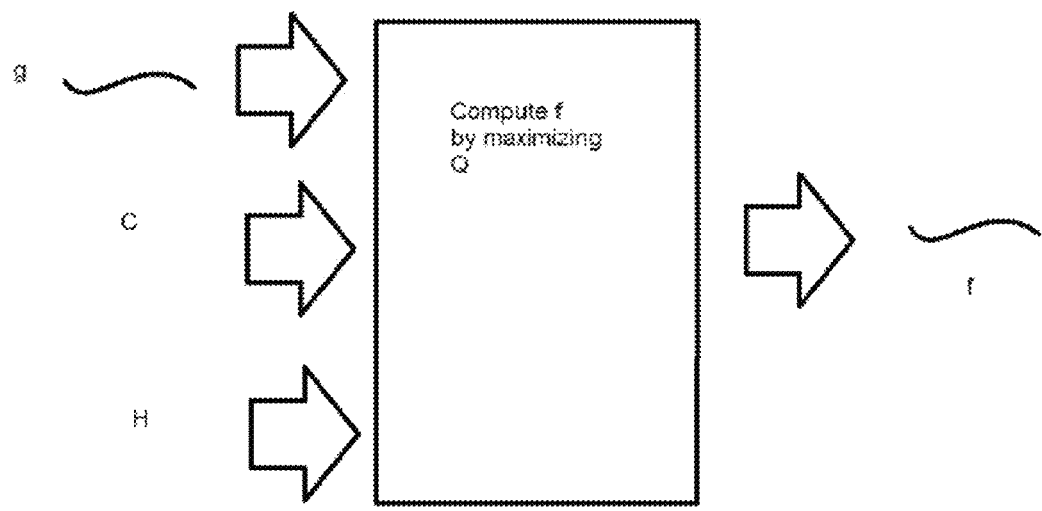
FIG. 1

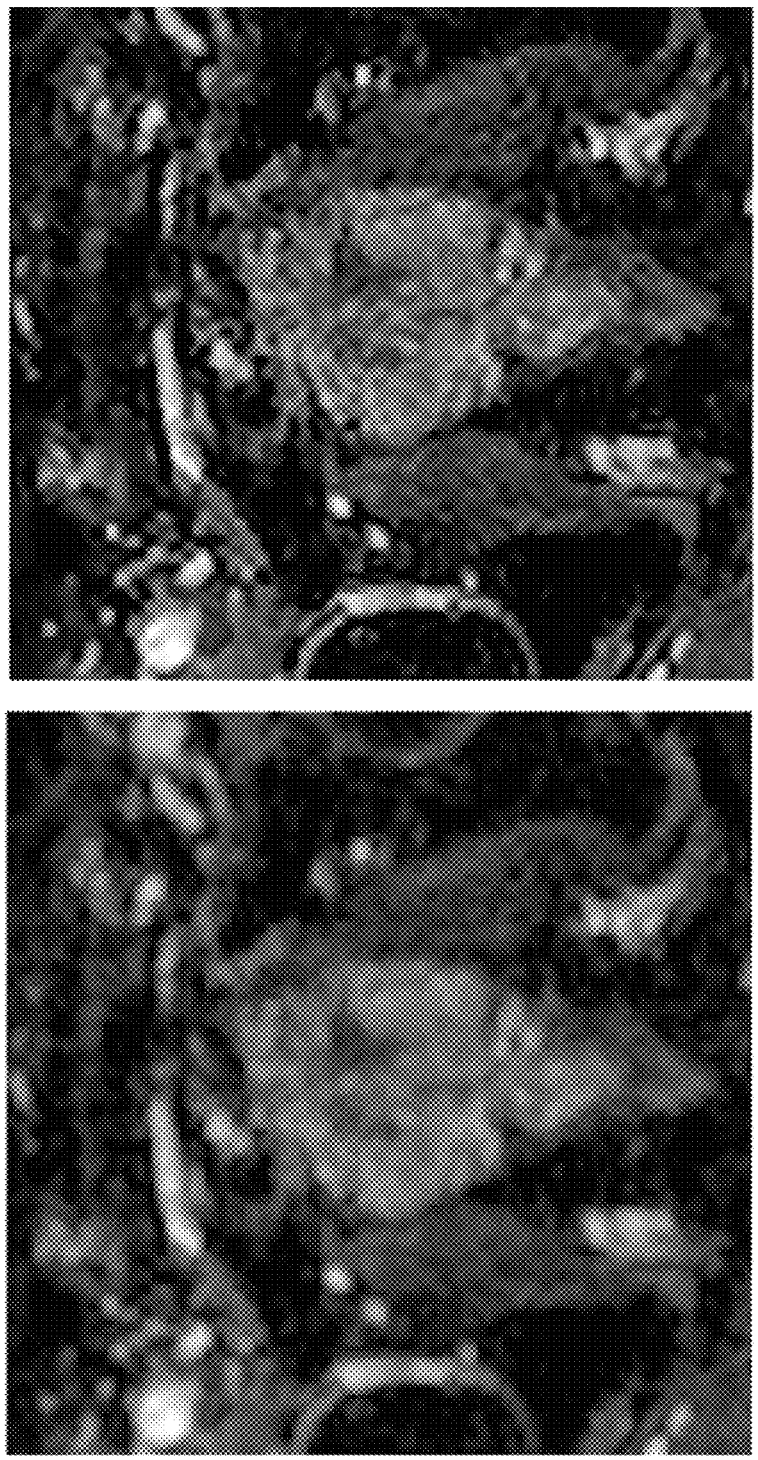

(b)

(a)

COMPENSATED MAGNETIC RESONANCE IMAGING SYSTEM AND METHOD FOR IMPROVED MAGNETIC RESONANCE IMAGING AND DIFFUSION IMAGING

FIELD OF THE INVENTION

The present invention relates generally to the field of magnetic resonance imaging, and more particularly to a system and method for improving image quality in magnetic resonance imaging and diffusion imaging utilizing improved imaging technologies and image processing techniques.

BACKGROUND

Magnetic resonance imaging (MRI) is an imaging technique often used in medical diagnostic applications in order to create detailed images of internal organs and internal physical features that cannot be obtained otherwise. For example, MRI may be used to image and diagnose neurological and cardiovascular diseases, as well as to assess the function and health of organs such as the prostate, liver, pancreas, and bile ducts. For oncology applications, as an illustrative example, T2-weighted MRI has been investigated for prostate cancer detection, but currently requires highly-qualified subspecialty radiologists to interpret the data due to its weak delineation between cancerous tissue and healthy tissue.

Diffusion weighted imaging (DWI) is a type of MRI in which pairs of opposing magnetic field gradient pulses are applied to obtain sensitivity to the Brownian motion of water molecules in tissues. The differences in diffusion characteristics between tissue types facilitate tissue characterization. As an example, DWI may be used for diagnosing prostate cancer which has a presumed high cellular density relative to the surrounding tissue. The cancerous tissues should therefore exhibit restricted diffusion characteristics (and as such should have lower apparent diffusion coefficient (ADC) values) relative to the surrounding tissue. While DWI is a promising imaging modality for diagnostic medical imaging, one of the key limitations associated with performing DWI for diagnosis is that the DWI imaging in current scanners is only achievable at a lower resolution and lower signal-to-noise ratio compared to the resolution and SNR that can be achieved using other MRI modalities such as T2-weighted imaging (T2w-MRI) using current scanners. This results in DWI images having lower image quality than is desirable.

Current techniques used to improve MRI image quality such as modifications to pulse sequences and acquisitions over a high number of excitations are either not feasible or not practical for use in DWI for medical diagnosis. More advanced techniques used for improving MRI image quality that is possible with DWI is multi-acquisition superresolution imaging, with has been applied to both T2w-MRI [1, 2, 3, 4] and DWI [5,6]. In multi-acquisition superresolution imaging, multiple MRI acquisitions are performed, and the resulting acquisitions are then combined to reconstruct an MRI image with higher effective resolution. However, multi-acquisition superresolution imaging necessitates multiple acquisitions of the same modality with the same settings (which increases scan times), as well as requiring complex imaging modifications and registration algorithms to properly align the multiple acquisitions together so that they can be combined. Another technique that can be used to improve MRI image quality for DWI is to reconstruct MRI images with high resolution from the lower-resolution MRI images using information from coplanar high resolution Mill images acquired of the same subject [7,8]. While this technique does not require multiple acquisitions of the same modality with the same settings, it relies on the additional acquisition of coplanar high resolution MRI images, as well as registration algorithms to properly align the coplanar high resolution MRI images to the low resolution MRI images for each patient acquisition, which can be difficult to achieve reliably and accurately. Another technique that also does not require multiple acquisitions of the same modality with the same settings are interpolation/inpainting methods [9, 10], where the low resolution MRI images are mapped into a higher resolution spatial domain grid and interpolation filters and inpainting methods are used to fill the gaps [9], or mapped into a higher resolution Fourier domain grid and then the high resolution image computed using the Fourier Transform [10]. While such methods improve MRI resolution, they do not improve or bring out tissue detail or contrast. Another technique for improving MRI image quality are methods that specifically remove undesirable "ghost" artifacts [11, 12]. While such methods are useful for ghost cancellation to improve such undesirable artifacts, they in general do not improve tissue detail or contrast in the MRI images. As such, an alternative form of improving image quality of magnetic resonance imaging that gets around these issues is highly desired, particularly for performing DWI for diagnosis of diseases such as cancer, as improving tissue detail and contrast is important for diagnostic purposes.

Therefore, what is needed are further improvements in MRI and DWI image quality utilizing novel imaging technologies and image processing techniques.

SUMMARY

The present invention relates to a system and method for improving the image quality of magnetic resonance imaging (MRI) and diffusion weighted imaging (DWI) utilizing improved imaging technologies and image processing techniques. More generally, the present system and method is designed to significantly improve the tissue detail and contrast of MRI images and DWI images in comparison to current technologies and techniques.

This disclosure describes a compensated magnetic resonance imaging (CMRI) system and method. With CMRI, during a calibration process, one or more test signals are acquired from an MRI system and, along with a baseline calibration signal, are used to determine a compensation function and a noise scale factor.

In an embodiment, a compensation function is determined during calibration by acquiring one or more test signals from an MRI system and finding a function that minimizes an error metric that takes a baseline calibration signal and the test signals transformed by the function as part of the input parameters. A noise scale factor is determined by using the acquired test signals by computing the noise statistics in homogeneous areas where the true signal intensities should be uniform in the test signals, and setting the noise scale factor based on the noise statistics.

In another embodiment, the compensation function and noise scale factor are determined together by minimizing an error metric that takes a noise-compensated baseline calibration signal and noise-compensated test signals transformed by the function as part of the input parameters.

Once a compensation function and a noise scale factor is determined for the MRI system, signal acquisitions are conducted from a subject, and the signals are then used to reconstruct MRI images at the same resolution or at a higher resolution by maximizing a quality metric, which quantifies the image quality of the reconstructed MRI images based on a specific criteria (i.e., a higher value for the quality metric indicates higher image quality), and takes the acquired signals, compensation function, and noise scale factor as part of the input parameters.

Advantageously, by taking into account a compensation function and a noise scale factor as part of the input parameters, CMRI can provide significantly improved MRI image quality and tissue detail and contrast in comparison to prior art systems and methods.

In another embodiment, the method comprises performing multiple signal acquisitions on a subject at different gradient pulse strengths and timings, then reconstructing diffusion-weighted imaging (DWI) images at the same resolution or at a higher resolution by maximizing a quality metric that takes the acquired signals, compensation function, and noise scale factor as part of the input parameters. The reconstructed DWI images are then used to compute the apparent diffusion coefficient (ADC) images, which can be utilized as an aid in the detection and localization of cancer.

In another embodiment, the method comprises performing multiple signal acquisitions on a subject at different gradient pulse strengths and timings, then reconstructing diffusion-weighted imaging (DWI) images at the same resolution or at a higher resolution by maximizing a quality metric that takes the acquired signals, compensation function, and noise scale factor as part of the input parameters. The reconstructed DWI images are then used to compute an interpolated or extrapolated DWI image with a different b-value, which can be utilized as an aid in the detection and localization of cancer.

In this respect, before explaining at least one embodiment of the invention in detail, it is to be understood that the invention is not limited in its application to the details of construction and to the arrangements of the components set forth in the following description or the examples provided therein, or illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

The present invention will be better understood and objects of the invention will become apparent when consideration is given to the following detailed description thereof. Such description makes reference to the annexed drawings wherein:

FIG. 1 shows an illustrative method of performing compensated magnetic resonance imaging (CMRI) in accordance with an embodiment;

FIG. 8(a) show illustrative results obtained from prior art digital imaging techniques, in comparison to FIG. 8(b) which shows an illustrative digital image of results produced using CMRI in accordance with embodiment;

Figure 2:
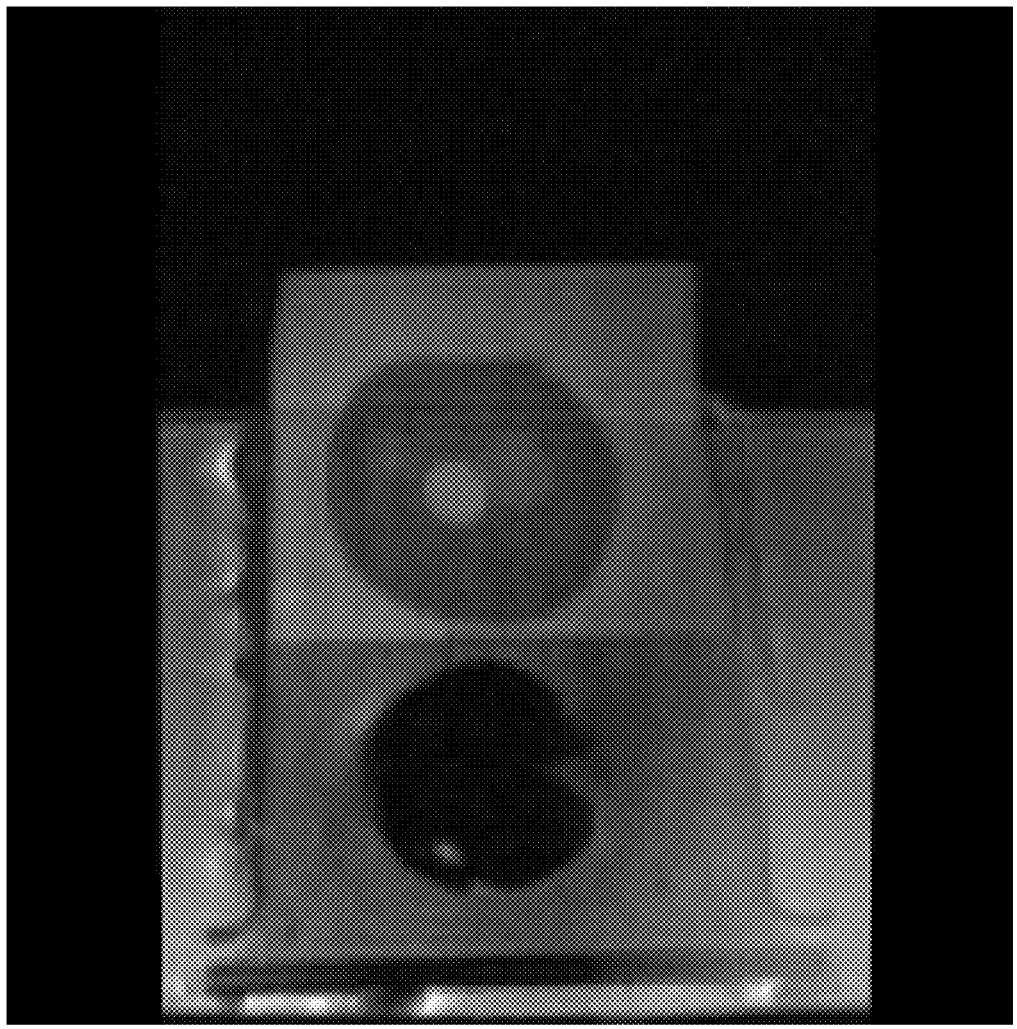
FIG. 2 shows an illustrative slice from a slice from a test signal acquisition of a test phantom object.

In the drawings, embodiments of the invention are illustrated by way of example. It is to be expressly understood that the description and drawings are only for the purpose of illustration and as an aid to understanding, and are not intended as a definition of the limits of the invention.

DETAILED DESCRIPTION

As noted above, the present invention relates to a system and method for improving the image quality of magnetic resonance imaging (MRI) and diffusion weighted imaging (DWI) utilizing improved imaging technologies and image processing techniques. In particular, the present system and method is designed to significantly improve the tissue detail and contrast that can be achieved in comparison to a conventional MRI and DWI techniques and technologies.

As will now be described in detail, a new system and method for improving MRI image quality and tissue detail and contrast is introduced and referred to in this disclosure as "compensated magnetic resonance imaging" or CMRI, which takes advantage of a compensation function and noise scale factor determined during an MRI calibration process to reconstruct MRI images acquired during the subject acquisition process with higher image quality and tissue detail and contrast without the need for performing multiple MRI acquisitions of the same modality with the same settings. Other embodiments of the presented system for computing Apparent Diffusion Coefficient (ADC) images with improved image quality and for computing interpolated and extrapolated DWI images with different b-values with improved image quality are also introduced. To the best of the inventor's knowledge, there are no previous imaging techniques that take this novel approach to improve MRI image quality. Illustrative embodiments of the system and method will now be described. First, the materials and methods underlying CMRI are described in the Method Section below.

Compensation Calibration Methodology

During a compensation calibration stage, one or more test signal acquisitions of a known test phantom object is performed on the MRI system. The test signals, along with a baseline calibration signal, are used to determine a compensation function and a noise scale factor.

During subject signal acquisition (which may be done independently of the compensation calibration stage), signal MRI acquisitions are obtained of a subject being imaged, and the signals are then used to reconstruct MRI images by maximizing a quality metric that takes the acquired signals, compensation function, and noise scale factor as part of the input parameters. An overview diagram of an embodiment of CMRI is shown in FIG. 1.

A detailed description of the steps involved in the methodology is presented below.

In an embodiment, a compensation calibration process is performed to determine a compensation function and noise scale factor for a particular configuration of the MRI system. First, a set of n test signal acquisitions (denoted as $T=\{t_1, t_2, t_3, \ldots, t_n\}$) of a test phantom object with known dimensions and characteristics are performed on the MRI system at that configuration, where n is a positive integer. An example slice from a test signal acquisition of a test phantom object is shown in FIG. 2. Given the set of acquired test signals T, and a baseline calibration signal based on the dimensions and characteristics of the test phantom object (denoted by l), a compensation function C is then determined by minimizing an error metric K that is a function of l, C, and T:

$$C = \mathrm{argmin}_C K(l, C, T)$$

The error metric K returns a real number that increases as the error increases, and decreases as the error increases. In an embodiment, the error metric K is set as the sum of squared error between l transformed by C and the set of test signals T:

$$K(l, C, T) = \Sigma_{i=1,2,\ldots,n} \Sigma_{j \in X} (C(l(\underline{x}_j)) - t_i(\underline{x}_j))^2$$

where X is the set of all positions in the signal, $\epsilon$ denotes "is an element of", $\underline{x}$ denotes position in the signal, $\underline{x}_j$ denotes the $j^{th}$ position, and $t_i$ is the $i^{th}$ test signal. In another embodiment, the error metric K is set as the negative conditional probability of C given l and T:

$$K(l, C, T) = -P(C | l, T)$$

where P denotes the conditional probability (based on system statistics and priors), and is equivalent to a Maximum a Posteriori (MAP) estimation of C. It will be appreciated, however, that the implementation of the present system and method is not limited to this particular error metric K, and other error metrics (such as sum of absolute error) may be used for K in other embodiments. In an embodiment, the compensation function C (operating on a signal u) can be set as:

$$C(u(\underline{x}_k)) = \Sigma_{i \in X} \gamma_{ik} u(\underline{x}_i)^{\alpha_{ik}} + \Sigma_{i \in X} \Sigma_{j \in X} \phi_{ijk} (u(\underline{x}_i) u)(\underline{x}_j))^{\beta_{ijk}}$$

where $\alpha_{ik}$ and $\gamma_{ik}$ are coefficients associated with positions i and j together, and $\beta_{ijk}$ and $\phi_{ijk}$ are coefficients associated with positions i, j, and k together. It will be appreciated, however, that the implementation of the present system and method is not limited to this particular form for compensation function C, and other forms of compensation functions (such as polynomial function form) may be used for C in other embodiments.

Given the set of test signals T, the noise statistics R for a set of M homogeneous areas where the true signal intensities should be uniform (denoted by $A_1, A_2, \ldots, A_M$) in the set of test signals T (identified using the baseline calibration signal l) are computed. In this embodiment, the noise statistics R is computed as set of second order moments $R = \{r_1, r_2, \ldots, r_M\}$:

$$r_j = E[t_j^2 | A_j] - (E[t_j | A_j])^2$$

where $E[t_j^2 | A_j]$ denotes the conditional expectation of the test signal $t_j$ given the $j^{th}$ area $A_j$, and $E[t_j^2 | A_j]$ denotes the conditional expectation of the squared test signal $t_j^2$ given the $j^{th}$ area $A_j$. It will be appreciated, however, that the implementation of the present system and method is not limited to this particular noise statistics R, and other noise statistics (such as third-order moments, fourth-order moments, etc.) may be used for K in other embodiments. The noise scale factor H is then determined based on R. In this embodiment, H is computed as a scalar multiple of the mean across the square roots of the elements of R:

$$H = (Z/M) \Sigma_{i \in R} \mathrm{sqrt}(r_i)$$

where sqrt(.) denotes square root and $r_i$ denotes the $i^{th}$ element of R, and Z is a scaling factor. It will be appreciated, however, that the implementation of the present system and method is not limited to this particular method for computing H, and other methods (such as median, mode, etc.) may be used to compute H in other embodiments.

In another embodiment, the compensation function C and noise scale factor H are determined together by minimizing an error metric K that takes a noise-compensated baseline calibration signal and noise-compensated test signals transformed by the function as part of the input parameters:

$$\{C, H\} = \mathrm{argmin}_{\{C, H\}} K(l, C, H, T)$$

The error metric K in this embodiment is set as the sum of squared error between l transformed by C and the test signals T processed by noise-compensation function W:

$$K(l, C, H, T) = \Sigma_{i=1,2,\ldots,n} \Sigma_{j \in X} (C(l(\underline{x}_j)) - W(t_j(\underline{x}_j), H))^2$$

where:

$$W(t(\underline{x}), H) = \{t(\underline{x}) \text{ if } t(\underline{x}) \geq H, \; 0 \text{ if } t(\underline{x}) < H\}$$

It will be appreciated, however, that the implementation of the present system and method is not limited to this particular method for computing C and H together, and other methods may be used to compute C and H together in other embodiments. Both C and H may be modified and adjusted by the technician after the calibration process.

Subject Signal Acquisition

Once the compensation function C and H have been computed for a particular configuration of the MRI machine during the compensation calibration stage, subject signal acquisition can take place using CMRI for this particular configuration or a similar configuration of the MRI machine at the same resolution or at a lower resolution than that used during the calibration stage. Note that C and H can be stored for that particular configuration and reused for all subsequent subject signal acquisitions at that particular configuration or a similar configuration without frequent recalibration at a later time.

Figure 3:
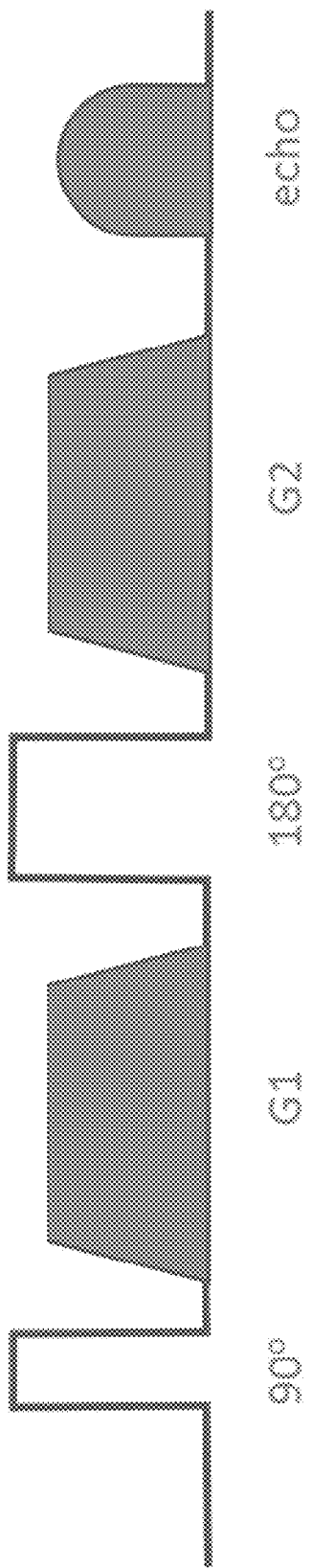
FIG. 3 shows an illustrative echo-planar sequence with two gradient pulses in accordance with an embodiment.
Figure 11B:
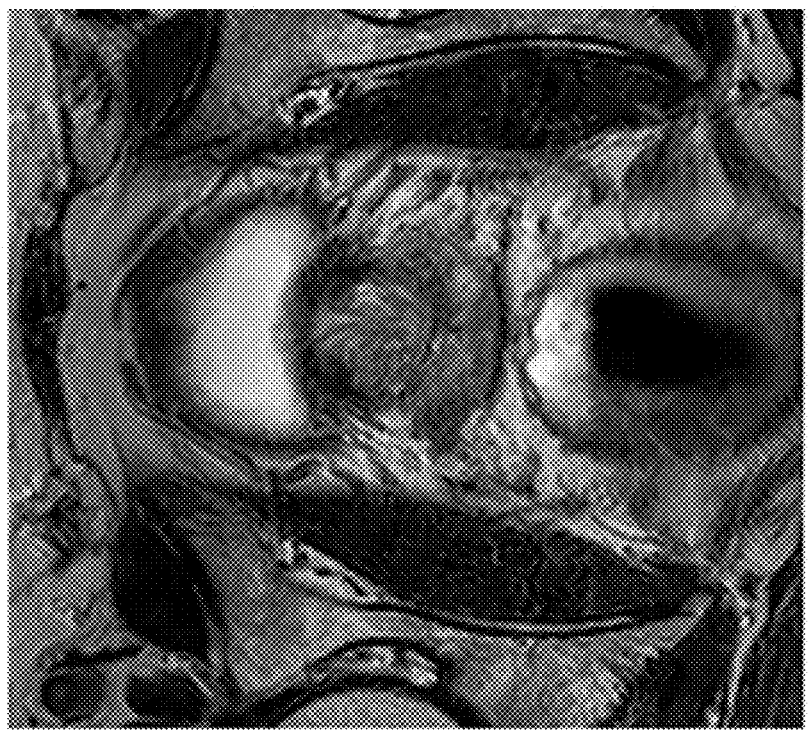
FIG. 11(a) show illustrative results obtained from prior art digital imaging techniques, in comparison to FIG. 11(b) which shows an illustrative digital image of results produced using CMRI in accordance with embodiment.
Figure 11A:
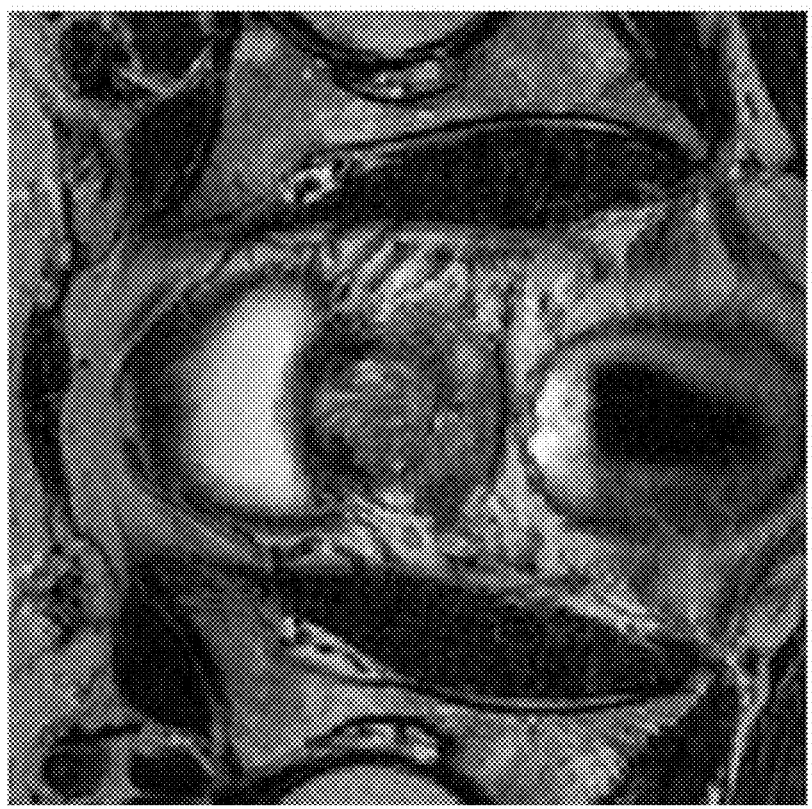

During subject signal acquisition, a signal MRI acquisition is conducted from a subject being imaged to obtain a MRI signal g. In an embodiment illustrating the performance of CMRI for improving DWI image quality, axial single-shot echo-planar sequences with two gradient pulses of equal magnitude (one pulse in each side of the 180° pulse to dephase and rephase the spins, respectively), as shown in FIG. 3 are used to obtain multiple DWI acquisitions using a set of different configurations of gradient pulse strengths and timings. It will be appreciated, however, that other sequences may be used in alternative embodiments, including for example multi-shot echo-planar sequences, interleaved echo-planar sequences, and spin-echo sequences, and that CMRI can be used for other MRI modalities such as T2-weighted MRI, as illustrated in FIG. 11. Given g, an CMRI-improved MRI signal f (at the same resolution or at a higher resolution by first mapping to a higher resolution grid before reconstruction) is reconstructed by maximizing a quality metric Q that takes the acquired signal g, compensation function C, and noise scale factor H as part of the input parameters:

$$f = \mathrm{argmax}_f Q(f, g, C, H)$$

In an embodiment, the quality metric Q is set as the conditional probability of f, given acquired signal g, compensation function C and noise scale factor H:

$$Q(f, g, C, H) = P(f | g, C, H)$$

where P denotes the conditional probability (based on system characteristics and priors), resulting in a Maximum a Posteriori (MAP) estimation of f. In another embodiment, the quality metric Q is the negative L2 error norm with total variation regularizer:

$$Q(f, g, C, H) = -(\|C(f) - g\|_2 + \lambda H \|\nabla f\|_1)$$

where $\|.\|_2$ denotes L2 error norm, $\nabla$ denotes gradient, and $\lambda$ is a scaling factor. In yet another embodiment, the quality metric Q is the negative L1 error norm with total variation regularizer:

$$Q(f, g, C, H) = -(\|C(f) - g\|_1 + \lambda H \|\nabla f\|_1)$$

where $\|.\|_1$ denotes L1 error norm, and $\nabla$ denotes gradient. It will be appreciated, however, that the implementation of the present system and method is not limited to these quality metrics for Q, and other quality metrics may be used for Q in other embodiments.

Apparent Diffusion Coefficient Image Computation using CMRI

Figure 4:
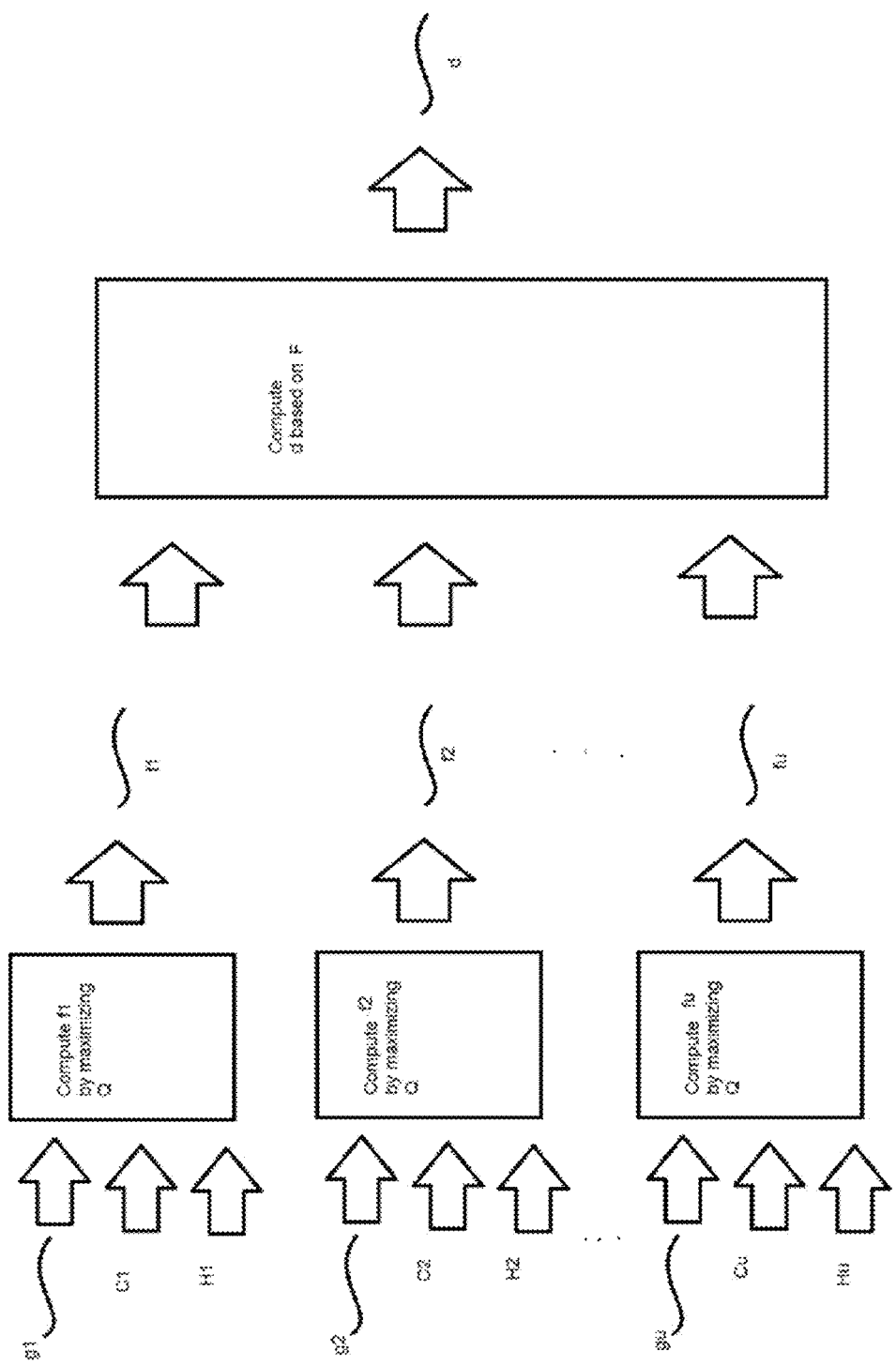
FIG. 4 is an illustrative example of a method of performing CMRI in accordance with another embodiment for reconstructing DWI images and then computing ADC images from the DWI images.

FIG. 4 is an illustrative example of a method of computing apparent diffusion coefficient (ADC) images using DWI images reconstructed using CMRI in accordance with another embodiment. In an embodiment, the method comprises performing multiple DWI acquisitions G={$g_1$, $g_2$, ... $g_u$} on a subject at different gradient pulse strengths and timings, then reconstructing diffusion-weighted imaging (DWI) images F={$f_1$, $f_2$, ..., $f_u$} by maximizing quality metric Q based on F, compensation functions ($C_1$, $C_2$, ..., $C_u$), and noise scale factors ($H_1$, $H_2$, ..., $H_u$). The reconstructed DWI images F are then used to compute the apparent diffusion coefficient (ADC) image d, which can be utilized as an aid in the detection and localization of cancer. In an embodiment, d is computed by maximizing the conditional probability of F given d (based on DWI relationship model used [13] (examples being monoexponential model and biexponential model for DWI formation)):

$$d = \mathrm{argmax}_d P(F | d)$$

This results in a Maximum Likelihood (ML) estimation of d. In another embodiment, d is computed using least squares estimation:

$$d = \mathrm{argmin}_d \Sigma_{i=1, 2, \ldots, u} \| f_i - S(b_i, d, f_{ref}, b_{ref}) \|_2$$

where $S(b, d, f_{ref}, b_{ref})$ is a function that returns an interpolated or extrapolated DWI image with a b-value of b based on the DWI relationship model used, given d, and a reference DWI image $f_{ref}$ with a b-value of $b_{ref}$ (from the set of reconstructed DWI images F). It will be appreciated, however, that the implementation of the present system and method is not limited to this particular method for computing d. Other methods may be used to compute d using the reconstructed DWI images F in other embodiments.

Interpolated or Extrapolated DWI Image Computation using CMRI

Figure 5:
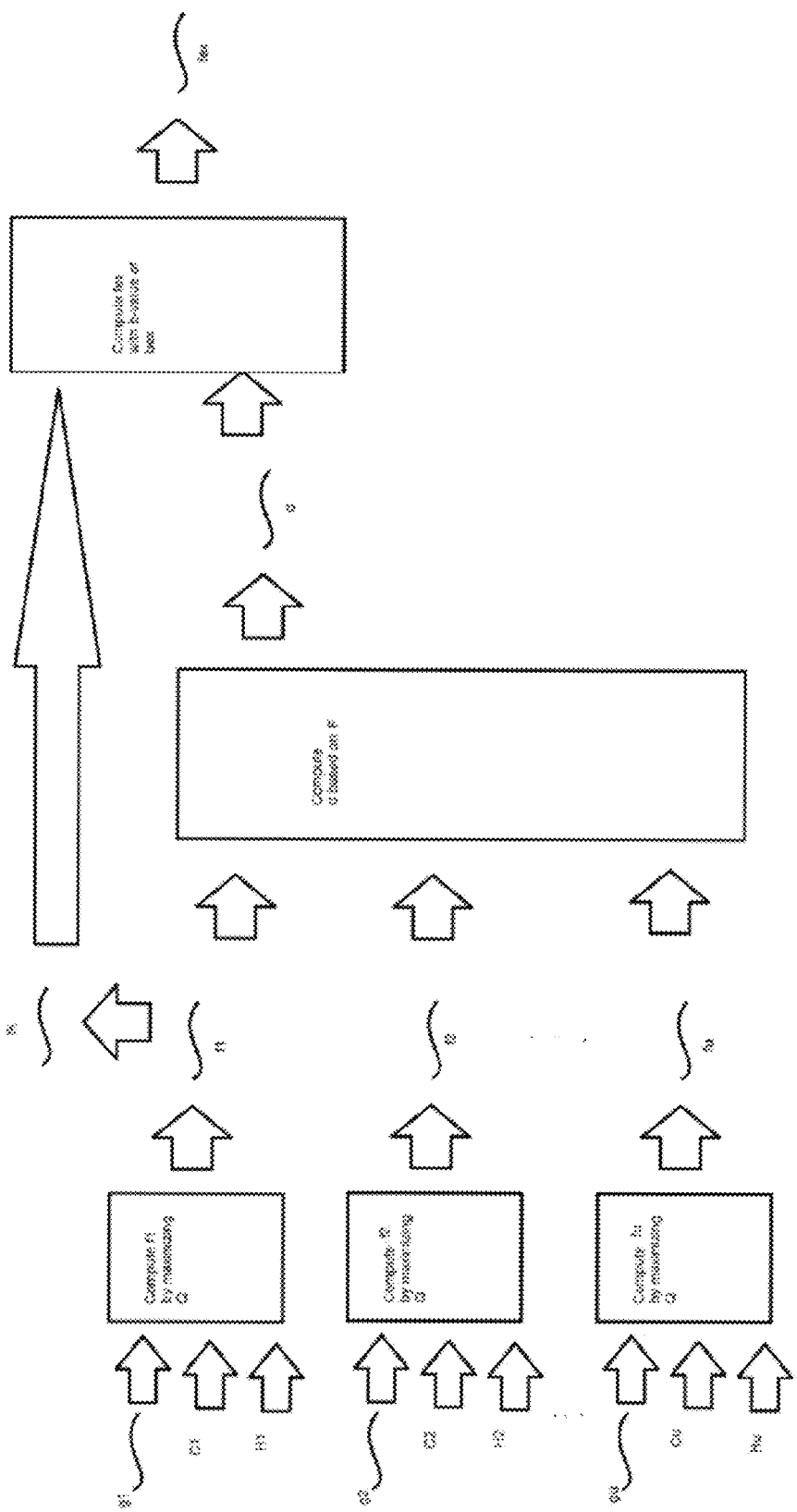
FIG. 5 is an illustrative example of a method of performing CMRI in accordance with another embodiment for reconstructing DWI images, then computing ADC images from the DWI images, and then computing interpolated or extrapolated DWI images at different b-values.

FIG. 5 is an illustrative example of a method of computing interpolated or extrapolated DWI images with different b-values using DWI images reconstructed using CMRI in accordance with another embodiment. In an embodiment, the method comprises performing multiple DWI acquisitions G={$g_1$, $g_2$, ... $g_u$} on a subject at different gradient pulse strengths and timings, then reconstructing diffusion-weighted imaging (DWI) images F={$f_1$, $f_2$, ..., $f_u$} by maximizing quality metric Q based on F, compensation functions ($C_1$, $C_2$, ..., $C_u$), and noise scale factors ($H_1$, $H_2$, ..., $H_u$). The reconstructed DWI images F are then used to compute the apparent diffusion coefficient (ADC) image d. Using d and one of the reconstructed DWI images from F (denoted here as $f_k$) with a b-value of $b_k$, an interpolated or extrapolated DWI image $f_{ex}$ with a b-value of $b_{ex}$ is computed using a DWI relationship model [13] (examples being monoexponential model and biexponential model for DWI relationship)). In this embodiment, the following equation is used to compute the interpolated or extrapolated DWI image using the monoexponential $$f_{ex} = f_k \exp((b_k - b_{ex}) d)$$

It will be appreciated, however, that the implementation of the present system and method is not limited to this particular method for computing $f_{ex}$, and other DWI relationship models (such as biexponential model) may be used to compute $f_{ex}$ in other embodiments.

Results

Figures 6A, 6B:
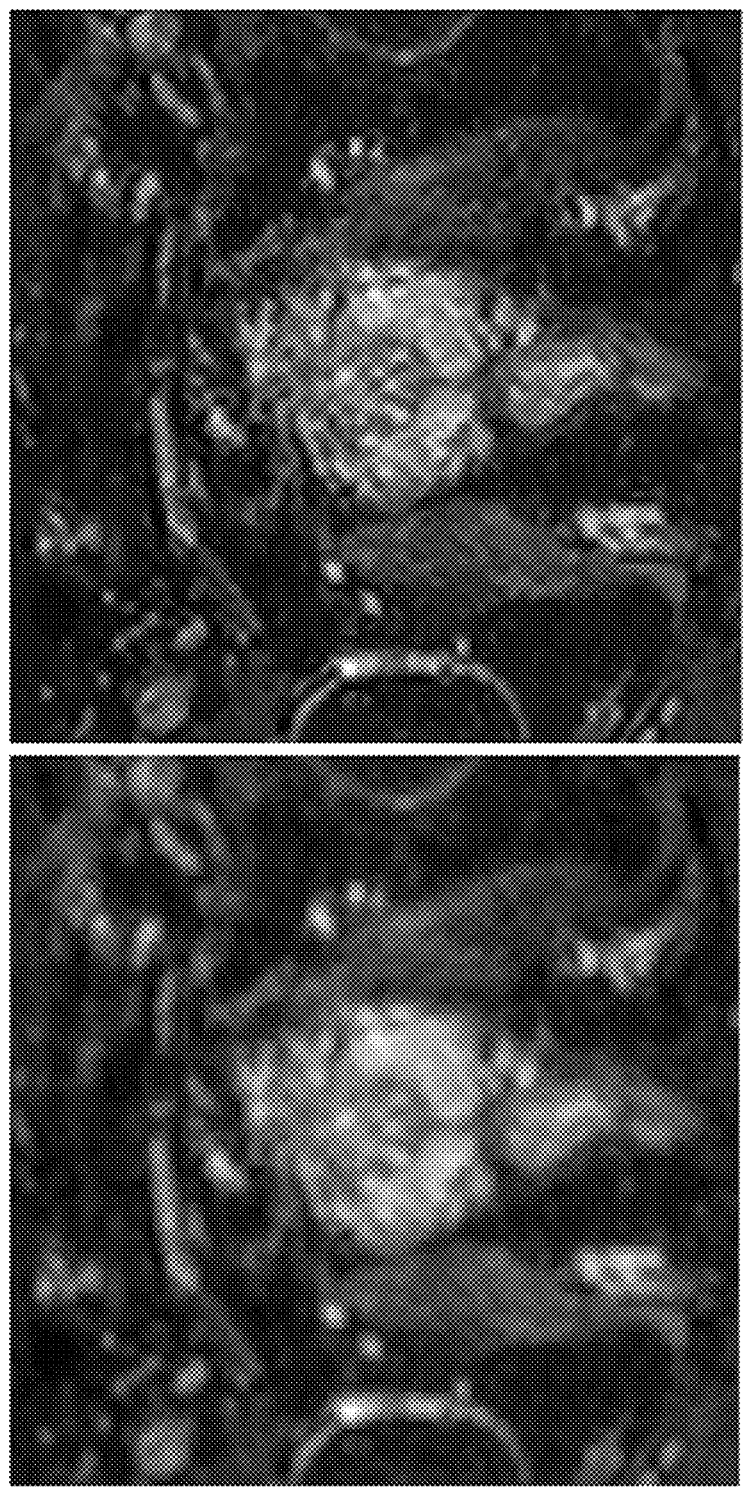
FIG. 6(a) show illustrative results obtained from prior art digital imaging techniques, in comparison to FIG. 6(b) which shows an illustrative digital image of results produced using CMRI in accordance with embodiment.
Figures 7A, 7B:
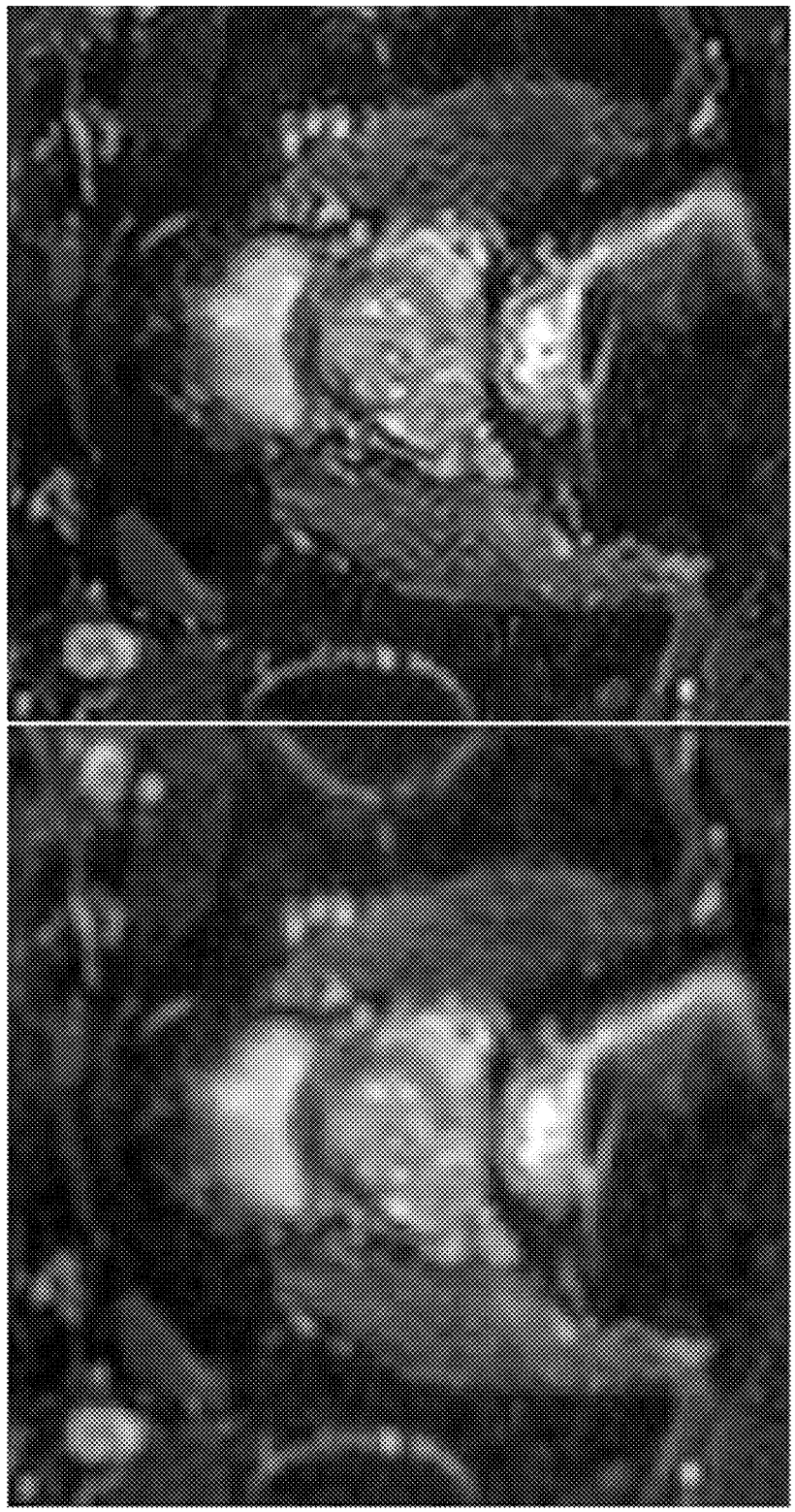
FIG. 7(a) show illustrative results obtained from prior art digital imaging techniques, in comparison to FIG. 7(b) which shows an illustrative digital image of results produced using CMRI in accordance with embodiment.
Figure 9B:
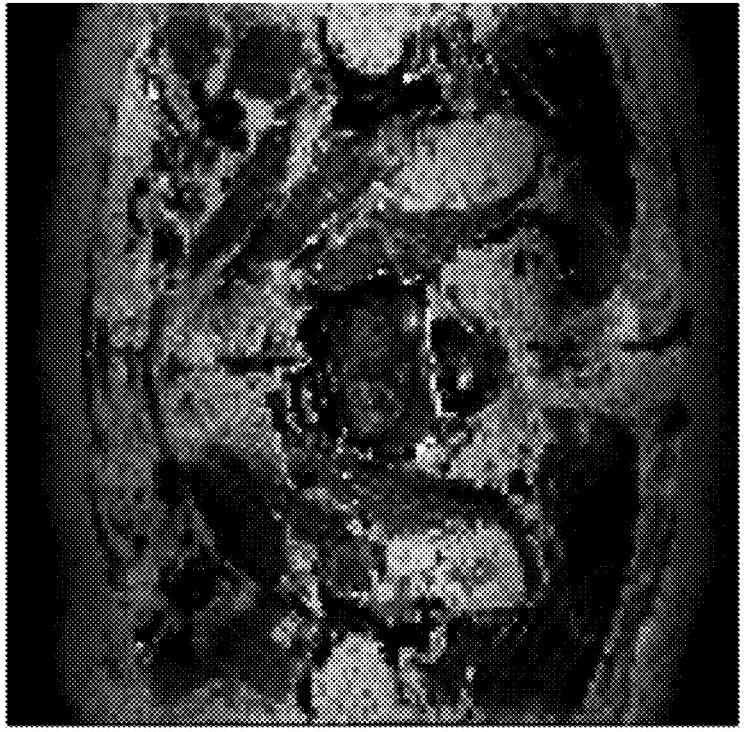
FIG. 9(a) show illustrative results obtained from prior art digital imaging techniques, in comparison to FIG. 9(b) which shows an illustrative digital image of results produced using CMRI in accordance with embodiment.
Figure 9A:
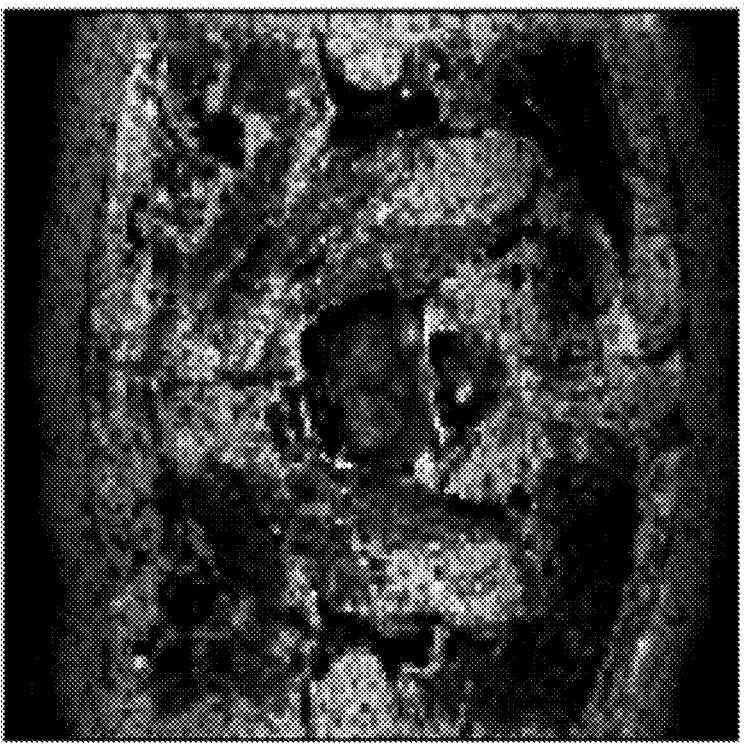
Figures 10A, 10B:
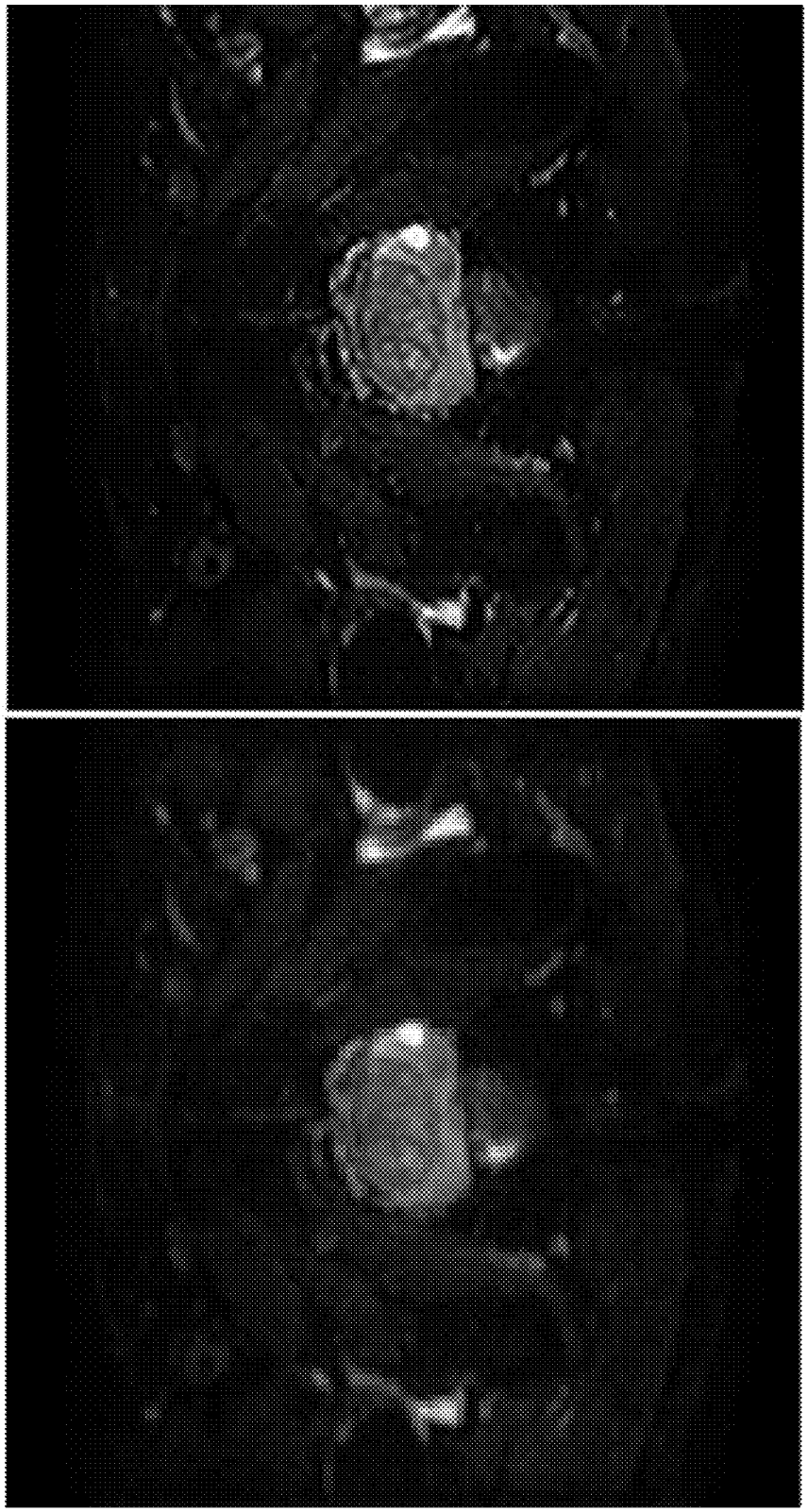
FIG. 10(a) show illustrative results obtained from prior art digital imaging techniques, in comparison to FIG. 10(b) which shows an illustrative digital image of results produced using CMRI in accordance with embodiment.

FIGS. 6(a)-6(b) and 7(a)-7(b) show illustrative examples of slices from DWI images achieved using a standard MRI system used for testing, and DWI images achieved using CMRI integrated into that same MRI system for two patient cases at Sunnybrook Health Sciences Centre. Informed consent was obtained from all patients, and approval for the study was obtained from the ethics review board of Sunnybrook Health Sciences Centre, located in Toronto, Canada. A number of observations can be made. The DWI results produced using the built-in approach has a blurry appearance, and does not show strong tissue contrast and detail. In contrast, the DWI results obtained from CMRI in accordance with the present invention is shown in FIG. 6(b) and FIG. 7(b). As can be seen, FIG. 6(b) and FIG. 7(b) has a sharper appearance and shows improved tissue contrast and detail. FIGS. 8(a)-8(b) show illustrative examples of slices from an ADC image achieved using the standard MRI system used for testing, and an ADC image achieved using CMRI. Once again, the ADC image produced using DWI images obtained from GMRI has a sharper appearance and has better tissue contrast and detail. FIGS. 9(a)-9(b) show illustrative examples of slices from a extrapolated DWI image with a b-value of 3000 s/mm² achieved using standard approach, and a extrapolated DWI image with a b-value of 3000 s/mm² achieved using CMRI. Once again, the extrapolated DWI image produced using DWI images obtained from CMRI has a higher SNR (less noisy), a sharper appearance and has better tissue contrast and detail. Hence, these experimental results are very promising and motivating for the potential of CMRI as a tool for improving ADC and extrapolated DWI image quality, which is important as ADC and extrapolated DWI are often used as a diagnostic tool for prostate cancer detection and localization. FIGS.

Figure 12:
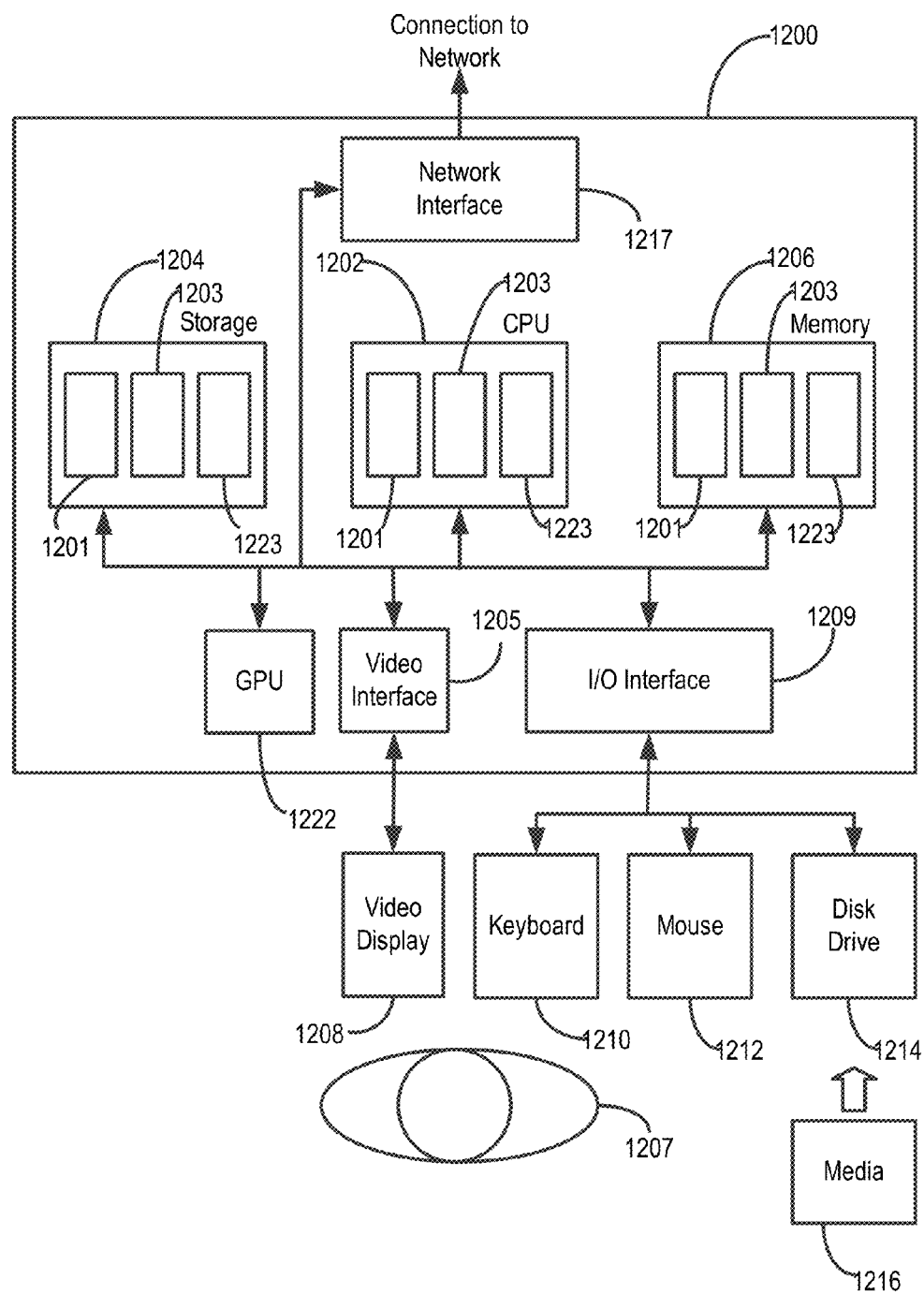
FIG. 12 shows an illustrative example of a generic computing device that may provide a suitable operating environment fir one or more embodiments.

10(*a*)-10(*b*) show illustrative examples of slices from a DWI image based on a low resolution acquisition achieved using the standard MRI system used for testing, and a high resolution DWI image achieved using CMRI based on a low resolution acquisition. The high-resolution DWI image obtained using CMRI has greater tissue detail and contrast and illustrates the CMRI's ability to generate high-resolution DWI images with improved tissue detail and contrast from a low resolution acquisition. FIGS. 11(*a*)-11(*b*) show illustrative examples of slices from a T2-weighted MRI image based on low resolution acquisitions achieved using the standard MRI system used for testing, and a high resolution T2-weighted MRI image achieved using CMRI based on low resolution acquisitions. The high-resolution T2-weighted MRI image obtained using GMRI has greater tissue detail and contrast and illustrates the CMRI's ability to generate high-resolution T2-weighted MRI images with improved tissue detail and contrast from a low resolution acquisition, Now referring to FIG. 12, shown is a schematic block diagram of a generic computing device. A suitably configured computer device, and associated communications networks, devices, software and firmware may provide a platform for enabling one or more embodiments as described above. By way of example, FIG. 12 shows a generic computer device 1200 that may include a central processing unit ("CPU") 1202 connected to a storage unit 1204 and to a random access memory 1206. The CPU 1202 may process an operating system 1201, application program 1203, and data 1223. The operating system 1201, application program 1203, and data 1223 may be stored in storage unit 1204 and loaded into memory 1206, as may be required. Computer device 1200 may further include a graphics processing unit (GPU) 1222 which is operatively connected to CPU 1202 and to memory 1206 to offload intensive image processing calculations from CPU 1202 and run these calculations in parallel with CPU 1202. An operator 1210 may interact with the computer device 1200 using a video display 1208 connected by a video interface 1205, and various input/output devices such as a keyboard 1210, pointer 1212, and storage 1214 connected by an I/O interface 1209. In known manner, the pointer 1212 may be configured to control movement of a cursor or pointer icon in the video display 1208, and to operate various graphical user interface (GUI) controls appearing in the video display 1208. The computer device 1200 may form part of a network via a network interface 1211, allowing the computer device 1200 to communicate with other suitably configured data processing systems or circuits. One or more different types of sensors 1230 connected via a sensor interface 1232 may be used to search for and sense input from various sources. The sensors 1230 may be built directly into the generic computer device 1200, or optionally configured as an attachment or accessory to the generic computer device 1200.

Thus, in an aspect, there is provided a method operable on a processing device, having a processor and a memory, for obtaining a magnetic resonance imaging (MRI) image from a MRI system, comprising: acquiring one or more test signals from a MRI system utilizing a test phantom object with known dimensions and characteristics; determining a compensation function that minimizes an error metric that takes a baseline calibration signal from the MRI system and the one or more acquired test signals transformed by the compensation function; determining a noise scale factor based on the plurality of acquired test signals by computing noise statistics in homogeneous areas where true signal intensities are substantially uniform in the one or more test signals; and utilizing the acquired test signals, the calculated compensation function, and the noise scale factor as input parameters to calculate an image quality metric.

In an embodiment, the method further comprises: acquiring a signal from a subject using an MRI system; reconstructing an MRI image of the MRI subject by maximizing the image quality metric; and displaying the reconstructed MRI image on a display.

In another embodiment, the method further comprises: acquiring the plurality of signals from the MRI subject at different gradient pulse strengths and timings; reconstructing a diffusion-weighted imaging (DWI) image of the MRI subject by maximizing the image quality metric; and displaying the reconstructed DWI image on a display.

In another embodiment, the method further comprises computing an apparent diffusion coefficient (ADC) image based on the reconstructed DWI image.

In another embodiment, the method further comprises computing an interpolated or extrapolated DWI image with a different b-value.

In another embodiment, the compensation function denoted by C is calculated by the following expression: $C=\text{argmin}_C K(l,C,T)$, where n test signals acquired with the test phantom object are denoted as $R=\{t_1, t_2, t_3, \ldots, t_n\}$, a baseline calibration signal based on the dimensions and characteristics of the test phantom object is denoted by l, and the error metric is denoted by K.

In another embodiment, the error metric K may be calculated by the following expression: $K(l,C,T)=\Sigma_{i=1,2,\ldots,n}\Sigma_{j\in X}(C(l(\underline{x}_j))-t_i(\underline{x}_j))^2$, where K is set as the sum of squared error between l transformed by C and the test signals T, and where $\underline{x}$ denotes position in the signal.

In another embodiment, the error metric K may be calculated by the following expression: $K(l,C,T)=-P(C|l,T)$, where P denotes the conditional probability based on system statistics and priors, and is equivalent to a Maximum a Posteriori (MAP) estimation of C.

In another embodiment, the compensation function C operating on a signal u can be set as: $C(u(\underline{x}_k))=\Sigma_{i\in X}\gamma_{ik}u(\underline{x}_i)^{\alpha_{ik}}+\Sigma_{i\in X}\Sigma_{j\in X}\phi_{ijk}(u(\underline{x}_i)u(\underline{x}_j))^{\beta_{ijk}}$, where X is the set of all positions, and $\alpha_{ik}$ and $\gamma_{ik}$ are coefficients associated with positions i and j together, and $\beta_{ijk}$ and $\phi_{ijk}$ are coefficients associated with positions i, j, and k together.

In another embodiment, the noise scale factor denoted by H is determined by noise statistics R calculated as a set of second order moments by the following expression: $R=\{r_1, r_2, \ldots, r_M\}$: $r_j=E[t_j^2|A_j]-(E[t_j|A_j])^2$, for a set of M homogeneous areas where the true signal intensities should be uniform denoted by $A_1, A_2, \ldots, A_M$ in the test signals, identified using the baseline calibration signal l. $E[t_j|A_j]$ denotes the conditional expectation of the test signal $t_j$ given the $j^{th}$ area $A_j$, and $E[t_j^2|A_j]$ denotes the conditional expectation of the squared test signal $t_j^2$ given the $j^{th}$ area $A_j$.

In another embodiment, the compensation function C and noise scale factor H are determined together by minimizing an error metric K that takes a noise-compensated baseline calibration signal and noise-compensated test signals transformed by the function as part of the input parameters: $\{C,H\}=\text{argmin}\{C,H\}K(l,C,H,T)$. The error metric K in this embodiment is set as the sum of squared error between l transformed by C and the test signals T processed by noise-compensation function W: $K(l,H,T)=\Sigma_{i=1,2,\ldots,n}\Sigma_{j\in X}(C(l(\underline{x}_j))-W(t_i(\underline{x}_j),H))^2$, where: $W(t(x),H)=\{t(x) \text{ if } t(x)>H, 0 \text{ if } t(x)\leq H\}$ In another embodiment, the method further comprises maximizing an image quality metric Q for an acquired signal g of an MRI subject is calculated by the following expression: $f=\text{argmax}_f Q(f,g,C,H)$, where the compensation function C, and noise scale factor H are part of the input parameters.

In another embodiment, the quality metric Q can be set as the conditional probability of f, given acquired signal g, compensation function C and noise scale factor H: $Q(f,g,C,H)=P(f|g,C,H)$, where P denotes the conditional probability (based on systems characteristics and prior information).

In another embodiment, the quality metric Q can be the negative L2 error norm with total variation regularizer: $Q(f,g,C,H)=-(\|C(f)-g\|_2+\lambda H\|\nabla f\|_1)$, where $\|.\|_2$ denotes L2 error norm, $\nabla$ denotes gradient, and $\lambda$ is a scaling factor.

In another embodiment, the quality metric Q can be the negative L1 error norm with total variation regularizer: $Q(f,g,C,H)=-(\|C(f)-g\|_1+\lambda H\|\nabla f\|_1)$, where $\|.\|_1$ denotes L1 error norm, and $\nabla$ denotes gradient.

In another embodiment, the method further comprises computing the ADC image comprises performing multiple DWI acquisitions $G=\{g_1, g_2, \ldots g_u\}$ on the MRI subject at different gradient pulse strengths and timings, then reconstructing DWI images $F=\{f_1, f_2, \ldots, f_u\}$ by maximizing quality metric Q based on F, compensation functions ($C_1, C_2, \ldots C_2$), and noise scale factors ($H_1, H_2, \ldots, H_u$).

In another aspect, here is provided a system for obtaining a magnetic resonance imaging (MRI) image from a MRI system, wherein the system is adapted to: acquire one or more test signals from a MRI system utilizing a test phantom object with known dimensions and characteristics; determine a compensation function that minimizes an error metric that takes a baseline calibration signal from the MRI system and the one or more acquired test signals transformed by the compensation function; determine a noise scale factor based on the plurality of acquired test signals by computing noise statistics in homogeneous areas where true signal intensities are substantially uniform in the one or more test signals; and utilize the acquired test signals, the calculated compensation function, and the noise scale factor as input parameters to calculate an image quality metric.

In an embodiment, the system is further adapted to: acquire a signal from a subject using an MRI system; reconstruct an MRI image of the MRI subject by maximizing the image quality metric; and display the reconstructed MRI image on a display.

In another embodiment, the system is further adapted to: acquire the plurality of signals from the MRI subject at different gradient pulse strengths and timings; reconstruct a diffusion-weighted imaging (DWI) image of the MRI subject by maximizing the image quality metric; and display the reconstructed DWI image on a display.

In another embodiment, the system is further adapted to: compute an apparent diffusion coefficient (ADC) image based on the reconstructed DWI image.

In another embodiment, the system is further adapted to compute an interpolated or extrapolated DWI image with a different b-value.

In another embodiment, the system is further adapted to calculate the compensation function denoted by C is calculated by the following expression: $C=\text{argmin}_C K(l,C,T)$, where n test signals acquired with the test phantom object are denoted as $T=\{t_1, t_2, t_3, \ldots, t_n\}$, a baseline calibration signal based on the dimensions and characteristics of the test phantom object is denoted by l, and the error metric is denoted by K.

In another embodiment, the error metric K may be calculated by the following expression: $K(l,C,T)=\Sigma i=1, 2, \ldots, n \Sigma \forall x(C(l(x))-ti(x))2$, where K is set as the sum of squared error between l transformed by C and the test signals T, and where x denotes position in the signal.

In another embodiment, the error metric K may be calculated by the following expression: $K(l,C,T)=\Sigma_{i=1,2,\ldots,n}\Sigma_{j\in X}(C(l(\underline{x}_j))-t_i(\underline{x}_j))^2$, where K is set as the sum of squared error between l transformed by C and the test signals T, and where x denotes position in the signal.

In another embodiment, the system is further adapted to set the compensation function C operating on a signal u can be set as: $C(u(\underline{x}_k))=\Sigma_{i\in X_{\gamma ik}}u(\underline{x}_i)^{\alpha_{ik}}+\Sigma_{i\in X}\Sigma_{j\in X\phi_{ijk}}(u(\underline{x}_i)u(\underline{x}_j))^{\beta_{ijk}}$, where X is the set of all positions, and $\alpha_{ik}$ and $\gamma_{ik}$ are coefficients associated with positions i and j together, and $\beta_{ijk}$ and $\phi_{ijk}$ are coefficients associated with positions i, j, and k together.

In another embodiment, the noise scale factor denoted by H is determined by noise statistics R calculated as a set of second order moments by the following expression: $R=\Delta r_1, r_2, \ldots, r_j=E[t_j^2|Aj]-(E[t_j|A_j])^2$, for a set of M homogeneous areas where the true signal intensities should be uniform denoted by $A_1, A_2, \ldots, A_M$ in the test signals, identified using the baseline calibration signal l, $E[t_j|A_j]$ denotes the conditional expectation of the test signal $t_j$ given the $j^{th}$ area $A_j$, and $E[t_j^2|A_j]$ denotes the conditional expectation of the squared test signal $t_j^2$ given the $j^{th}$ area $A_j$.

In another embodiment, the compensation function C and noise scale factor FT are determined together by minimizing an error metric K that takes a noise-compensated baseline calibration signal and noise-compensated test signals transformed by the function as part of the input parameters: $\{C,H\}=\text{argmin}\{C,H\} K(l,C,H,T)$. The error metric K in this embodiment is set as the sum of squared error between l transformed by C and the test signals T processed by noise-compensation function W: $K(l,C,H,T)=\Sigma_{i=1,2,\ldots,n}\Sigma_{j\in X}(C(l(\underline{x}_j))-W(t_i(\underline{x}_j),H))^2$, where: $W(t(x),H)=\{t(x) \text{ if } t(x)>H, 0 \text{ if } t(x)<H\}$ In another embodiment, the system is further adapted to maximize an image quality metric Q for an acquired signal g of an MRI subject is calculated by the following expression: $f=\text{argmax}_f Q(f,g,C,H)$, where the compensation function C, and noise scale factor H are part of the input parameters.

In another embodiment, the quality metric Q can be set as the conditional probability of f, given acquired signal g, compensation function C and noise scale factor H: $Q(f,g,C,H)=P(f|g,C,H)$, where P denotes the conditional probability (based on systems characteristics and prior information).

In another embodiment, the quality metric Q can be the negative L2 error norm with total variation regularizer: $Q(f,g,C,H)=-(\|C(f)-g\|_2+\lambda H\|\nabla f\|_1)$, where $\|.\|_2$ denotes L2 error norm, $\nabla$ denotes gradient, and $\lambda$ is a scaling factor.

In another embodiment, the quality metric Q can be the negative L1 error norm with total variation regularizer: $Q(f,g,C,H)=-(\|C(f)-g\|_1+\lambda H\|\nabla f\|_1)$, where $\|.\|_2$ denotes L1 error norm, and $\nabla$ denotes gradient.

In another embodiment, the system is adapted to compute the ADC image comprises performing multiple DWI acquisitions $G=\{g_1, g_2, \ldots g_u\}$ on the MRI subject at different gradient pulse strengths and timings, then reconstructing DWI images $F=\{f_1, f_2, \ldots, f_u\}$ by maximizing quality metric Q based on F, compensation functions ($C_1, C_2, \ldots, C_u$), and noise scale factors ($H_1, H_2, \ldots, H_u$), While illustrative embodiments have been described above by way of example, it will be appreciated that various changes and modifications may be made without departing from the scope of the invention, which is defined by the following claims.

REFERENCES

[1] Greenspan H. MRI inter-slice reconstruction using super-resolution. Magn. Res. Imag. 2002; 20(5):437-446.

[2] Greenspan H. Super-Resolution in Medical Imaging. Comput. J. 2009; 52(1):43-63.

[3] E. Carmi, S. Liu, N. Alon, A. Fiat, and D. Fiat, Resolution enhancement in MRI. Magnetic Resonance Imaging, 2006; 24(2): 133-154.

[4] Peled S, Yeshurun Y. Superresolution in MRI: application to human white matter fiber tract visualization by diffusion tensor imaging. Magn. Res. in Med. 2001; 45(1): 29-35.

[5] Scherrer, B., Gholipour, A., and Warfieid S. Super-Resolution in Diffusion-Weighted Imaging. Med Image Comput Comput Assist Interv. 2011; 14(0 2): 124-132.

[6] Komprobst, P., Peelers, R., Nikolova, M., Deriche, R., Ng, M., and Van Hecke, P. A superresolution framework for fMRI sequences and its impact on resulting activation maps. Proceedings 6th International Conference Medical Image Computing and Computer-Assisted intervention (MICCAI '03), 2013; 2879:117-125.

[7] Rousseau, F. Brain hallucination. Proceedings of the European Conference on Computer Vision (ECCV '08), LNCS, pp. 497-508, Springer, New York, N.Y., USA, 2008.

[8] Manjon, J., Coupé, P., Buades, A., Collins, D., and Robles, M. MRI Superresolution Using Self Similarity and Image Priors. Article ID 425891, International Journal of Biomedical Imaging 2010.

[9] Souza, A., Senn R. Method for enhanced voxel resolution in MRI image. Patent EP20090000249, 2011.

[10] Li, J. Resizing MRI images using fourier transformation. U.S. Pat. No. 5,036,281, 1991.

[11] Kellman P., McVeigh E. Ghost Artifact Cancellation Using Phased Array Processing. U.S. Pat. No. 6,771,067, 2001.

[12] Kellman P., McVeigh E. Method and apparatus to improve an MRI image using regularization. U.S. Pat. No. 7,154,268.

[13] Glaister, J., Cameron, A., Wong, A., and Haider, M. A., Quantitative investigative analysis of tumour separability in the prostate gland using ultra-high b-value computed diffusion imaging. Engineering in Medicine and Biology Society (EMBC), 2012 Annual International Conference of the IEEE. 2012; 420-423.

The invention claimed is:

1. A method operable on a processing device, having a processor and a memory, for improving the quality of a magnetic resonance imaging (MRI) image obtained from a MRI system, comprising:

acquiring one or more test signals from a MRI system utilizing a test phantom object with known dimensions and characteristics;

determining a compensation function C that minimizes an error metric that takes a baseline calibration signal from the MRI system and the one or more acquired test signals transformed by the compensation function C, the compensation function C calculated by the following expression:

$$C = \mathrm{argmin}\, CK(l,C,T);$$

where n test signals acquired with the test phantom object are denoted as $T=\{t1, t2, t3, \ldots, tn\}$, a baseline calibration signal based on the dimensions and characteristics of the test phantom object is denoted by I, and the error metric is denoted by K;

determining a noise scale factor based on the plurality of acquired test signals by computing noise statistics in homogeneous areas where true signal intensities are substantially uniform in the one or more test signals;

utilizing the acquired test signals, the calculated compensation function, and the noise scale factor as input parameters to calculate an image quality metric;

acquiring a signal from a subject using the MRI system;

reconstructing an MRI image of the MRI subject by maximizing the image quality metric; and displaying the reconstructed MRI image on a display.

2. The method claim 1, further comprising:

acquiring the plurality of signals from the MRI subject at different gradient pulse strengths and timings;

reconstructing a diffusion-weighted imaging (DWI) image of the MRI subject by maximizing the image quality metric; and displaying the reconstructed DWI image on a display.

3. The method of claim 2, further comprising computing an apparent diffusion coefficient (ADC) image based on the reconstructed DWI image.

4. The method of claim 2, further comprising computing an interpolated or extrapolated DWI image with a different b-value.

5. The method of claim 1, wherein the error metric K may be calculated by the following expression:

$$K(l,C,T) = \Sigma i = 1,2, \ldots, n \Sigma j \epsilon X(C(l(xj)) - ti(xj))2$$

where K is set as the sum of squared error between l transformed by C and the test signals T, and where x denotes position in the signal.

6. The method of claim 1, wherein the error metric K may be calculated by the following expression:

$$K(l,C,T) = -P(C|l,T)$$

where P denotes the conditional probability based on system statistics and priors, and is equivalent to a Maximum a Posteriori (MAP) estimation of C.

7. The method of claim 1, wherein the compensation function C operating on a signal u can be set as:

$$C(u(xk)) = \Sigma i \epsilon X \gamma i k u(xi) \alpha i k + \Sigma i \epsilon X \Sigma j \epsilon X \phi i j k (u(xi) u)(xj)) \beta ijk$$

where X is the set of all positions, and αik and γik are coefficients associated with positions i and j together, and βijk and φijk are coefficients associated with positions i, j, and k together.

8. The method of claim 1, wherein the noise scale factor denoted by H is determined by noise statistics R calculated as a set of second order moments by the following expression:

$$R = \{r1, r2, \ldots, rM\}:\ rj = E[tj2|Aj] - (E[tj|Aj])2$$

for a set of M homogeneous areas where the true signal intensities should be uniform denoted by A1, A2, ..., AM in the test signals, identified using the baseline calibration signal l, E[tj|Aj] denotes the conditional expectation of the test signal tj given the jth area Aj, and E[tj2|Aj] denotes the conditional expectation of the squared test signal tj2 given the jth area Aj.

9. The method of claim 1, wherein the compensation function C and noise scale factor H are determined together by minimizing an error metric K that takes a noise-compensated baseline calibration signal and noise-compensated test signals transformed by the function as part of the input parameters:

$$\{C,H\} = \mathrm{argmin}\{C,H\} K(l,C,H,T)$$

wherein, the error metric K is set as the sum of squared error between I transformed by C and the test signals T processed by noise-compensation function W:

$$K(l,C,H,T)=\Sigma i=1,2,\ldots,n\Sigma j\in X(C(l(xj))-W(tj(xj),H))2$$

where:

$$W(t(x),H=\{t(x) \text{ if } t(x)>H, 0 \text{ if } t(x)<H\}$$

10. The method of claim 1, wherein maximizing an image quality metric Q for an acquired signal g of an MRI subject is calculated by the following expression:

$$f=\text{argmax} fQ(f,g,C,H)$$

where the compensation function C, and noise scale factor H are part of the input parameters.

11. The method of claim 10, wherein the quality metric Q can be set as the conditional probability of f, given acquired signal g, compensation function C and noise scale factor H:

$$Q(f,g,C,H)=P(f|g,C,H)$$

where P denotes the conditional probability (based on systems characteristics and prior information).

12. The method of claim 10, wherein the quality metric Q can be the negative L2 error norm with total variation regularizer:

$$Q(f,g,C,H)=-(\|C(f)-g\|2+\lambda H\|\nabla f\|1)$$

where $\|.\|2$ denotes L2 error norm, $\nabla$ denotes gradient, and $\lambda$ is a scaling factor.

13. The method of claim 10, wherein the quality metric Q can be the negative L1 error norm with total variation regularizer:

$$Q(f,g,C,H)=-(\|C(f)-g\|1+\lambda H\|\nabla f\|1)$$

where $\|.\|1$ denotes L1 error norm, and $\nabla$ denotes gradient.

14. The method of claim 3, wherein computing the ADC image comprises performing multiple DWI acquisitions $G=\{g1, g2, \ldots gu\}$ on the MRI subject at different gradient pulse strengths and timings, then reconstructing DWI images $F=\{f1, f2, \ldots, fu\}$ by maximizing quality metric Q based on F, compensation functions (C1, C2, ..., Cu), and noise scale factors (H1, H2, ..., Hu).

15. A system for improving the quality of a magnetic resonance imaging (MRI) image obtained from a MRI system, wherein the system is adapted to:
acquire one or more test signals from a MRI system utilizing a test phantom object with known dimensions and characteristics;
determine a compensation function C that minimizes an error metric that takes a baseline calibration signal from the MRI system and the one or more acquired test signals transformed by the compensation function C, the compensation function C calculated by the following expression:

$$C=\text{argmin} CK(l,C,T);$$

where n test signals acquired with the test phantom object are denoted as $T=\{t1, t2, t3, \ldots, tn\}$, a baseline calibration signal based on the dimensions and characteristics of the test phantom object is denoted by I, and the error metric is denoted by K;
determine a noise scale factor based on the plurality of acquired test signals by computing noise statistics in homogeneous areas where true signal intensities are substantially uniform in the one or more test signals;
utilize the acquired test signals, the calculated compensation function, and the noise scale factor as input parameters to calculate an image quality metric;
acquire a signal from a subject using the MRI system;
reconstruct an MRI image of the MRI subject by maximizing the image quality metric; and
display the reconstructed MRI image on a display.

16. The system of claim 15, wherein the system is further adapted to:
acquire the plurality of signals from the MRI subject at different gradient pulse strengths and timings;
reconstruct a diffusion-weighted imaging (DWI) image of the MRI subject by maximizing the image quality metric; and
display the reconstructed DWI image on a display.

17. The system of claim 16, wherein the system is further adapted to compute an apparent diffusion coefficient (ADC) image based on the reconstructed DWI image.

18. The system of claim 16, wherein the system is further adapted to compute an interpolated or extrapolated DWI image with a different b-value.

19. The system of claim 15, wherein the error metric K may be calculated by the following expression:

$$K(l,C,T)=\Sigma i-1,2,\ldots n\Sigma j\in X(C(l(xj))-ti(xj))2$$

where K is set as the sum of squared error between l transformed by C and the test signals T, and where x denotes position in the signal.

20. The system of claim 1, wherein the error metric K may be calculated by the following expression:

$$K(l,C,T)=-P(C|l,T)$$

where P denotes the conditional probability based on system statistics and priors, and is equivalent to a Maximum a Posteriori (MAP) estimation of C.

21. The system of claim 1, wherein the compensation function C operating on a signal u can be set as:

$$C(u(xk))=\Sigma i\in X\gamma iku(xi)\alpha ik+\Sigma i\in X\Sigma j\in X\phi ijk(u(xi)u)(xj))$$
$$\beta ijk$$

where X is the set of all positions, and $\alpha ik$ and $\gamma ik$ are coefficients associated with positions i and j together, and $\beta ijk$ and $\phi ijk$ are coefficients associated with positions i, j, and k together.

22. The system of claim 15, wherein the noise scale factor denoted by H is determined by noise statistics R calculated as a set of second order moments by the following expression:

$$R=\{r1,r2,\ldots,rM\}: rj=E[tj2|Aj]-(E[tj|Aj])2$$

for a set of M homogeneous areas where the true signal intensities should be uniform denoted by A1, A2, ..., AM in the test signals, identified using the baseline calibration signal l, $E[tj|Aj]$ denotes the conditional expectation of the test signal tj given the jth area Aj, and $E[tj2|Aj]$ denotes the conditional expectation of the squared test signal tj2 given the jth area Aj.

23. The system of claim 15, wherein the compensation function C and noise scale factor H are determined together by minimizing an error metric K that takes a noise-compensated baseline calibration signal and noise-compensated test signals transformed by the function as part of the input parameters:

$$\{C,H\}=\text{argmin}\{C,H\}K(l,C,H,T)$$

The error metric K in this embodiment is set as the sum of squared error between l transformed by C and the test signals T processed by noise-compensation function W:

$$K(l,C,T) = \Sigma i=1,2,\ldots,n \Sigma j \in X(C(l(xj))-ti(xj))2$$

$$W(t(x),H) = \{t(x) \text{ if } t(x) > H, 0 \text{ if } t(x) < H\}.$$

24. The system of claim 15, wherein maximizing an image quality metric 0 for an acquired signal g of an MRI subject is calculated by the following expression:

$$f = \text{argmax} f Q(f,g,C,H)$$

where the compensation function C, and noise scale factor H are part of the input parameters.

25. The system of claim 24, wherein the quality metric Q can be set as the conditional probability of f, given acquired signal g, compensation function C and noise scale factor H:

$$Q(f,g,C,H) = P(f|g,C,H)$$

where P denotes the conditional probability (based on systems characteristics and prior information).

26. The system of claim 24, wherein the quality metric Q can be the negative L2 error norm with total variation regularizer:

$$Q(f,g,C,H) = -(\|C(f)-g\|2 + \lambda H \|\nabla f\|1)$$

where $\|.\|2$ denotes L2 error norm, $\nabla$ denotes gradient, and $\lambda$ is a scaling factor.

27. The system of claim 24, wherein the quality metric Q can be the negative L1 error norm with total variation regularizer:

$$Q(f,g,C,H) = -(\|C(f)-g\|1 + \lambda H \|\nabla f\|1)$$

where $\|.\|1$ denotes L1 error norm, and $\nabla$ denotes gradient.

28. The system of claim 17, wherein computing the ADC image comprises performing multiple DWI acquisitions $G = \{g1, g2, \ldots gu\}$ on the MRI subject at different gradient pulse strengths and timings, then reconstructing DWI images $F = \{f1, f2, \ldots, fu\}$ by maximizing quality metric Q based on F, compensation functions (C1, C2, ..., Cu), and noise scale factors (H1, H2, ..., Hu).

* * * * *